United States Patent
Erbel et al.

(10) Patent No.: US 6,865,411 B2
(45) Date of Patent: Mar. 8, 2005

(54) PATIENT POSITIONING SYSTEM FOR RADIOTHERAPY

(75) Inventors: Stephan Erbel, München (DE); Stephan Fröhlich, Aschheim (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 221 days.

(21) Appl. No.: 09/949,294

(22) Filed: Sep. 7, 2001

(65) Prior Publication Data

US 2002/0120986 A1 Sep. 5, 2002

(30) Foreign Application Priority Data

Mar. 5, 2001 (EP) ............................................. 01104553
Jun. 6, 2001 (EP) ............................................. 01112942

(51) Int. Cl.[7] ................................................. A61B 5/05
(52) U.S. Cl. ..................................................... 600/407
(58) Field of Search ............................... 600/407–472; 128/989; 378/4, 65, 63, 21, 69, 16, 195, 177, 193, 19, 901, 209; 5/601

(56) References Cited

U.S. PATENT DOCUMENTS

| | | | |
|---|---|---|---|
| 3,818,516 A | | 6/1974 | Hopper et al. |
| 4,905,267 A | | 2/1990 | Miller et al. |
| 5,117,445 A | * | 5/1992 | Seppi et al. ............. 378/65 |
| 5,475,884 A | | 12/1995 | Kirmse et al. |
| 5,651,043 A | * | 7/1997 | Tsuyuki et al. ........... 378/65 |
| 5,754,623 A | * | 5/1998 | Seki ......................... 378/65 |
| 5,851,182 A | | 12/1998 | Sahadevan |
| 6,405,072 B1 | * | 6/2002 | Cosman ................. 600/426 |
| 2002/0095730 A1 | * | 7/2002 | Al-Kassim et al. ........ 5/601 |

FOREIGN PATENT DOCUMENTS

| | | |
|---|---|---|
| DE | 2 260 140 A | 6/1974 |
| DE | 43 41 779 A | 6/1995 |
| DE | 196 12 091 A | 3/1997 |
| DE | 199 20 008 A | 12/2000 |
| EP | 0 047 958 | 3/1982 |
| EP | 0 370 567 | 5/1990 |
| EP | 0 562 585 | 9/1993 |
| WO | 99/27839 | 6/1999 |

* cited by examiner

*Primary Examiner*—Ali Imam
(74) *Attorney, Agent, or Firm*—Renner, Otto, Boisselle & Sklar LLP

(57) ABSTRACT

The invention concerns a patient positioning system for radiotherapy, comprising a device for positioning a patient within the framework of treatment planning, using image detection and/or carrying out radiation treatment, comprising a patient bed (3, 42, 50) on which a patient is positioned, wherein means are provided by which the same bed (3, 42, 50) may be arranged both on a planning couch (8) for image detection within the framework of treatment planning as well as on a radiotherapy table (1, 44), and by providing a reference means (54) on the patient bed by which the position of the immobilized patient or of a marked radiation target is determined with respect to the patient bed (3, 42, 50). Within this framework, a corresponding method is also provided, as well as an adjusting means for the transport and the bed.

26 Claims, 5 Drawing Sheets

Position 1        Position 2

PATIENT POSITIONING SYSTEM FOR RADIOTHERAPY

Figure 10:
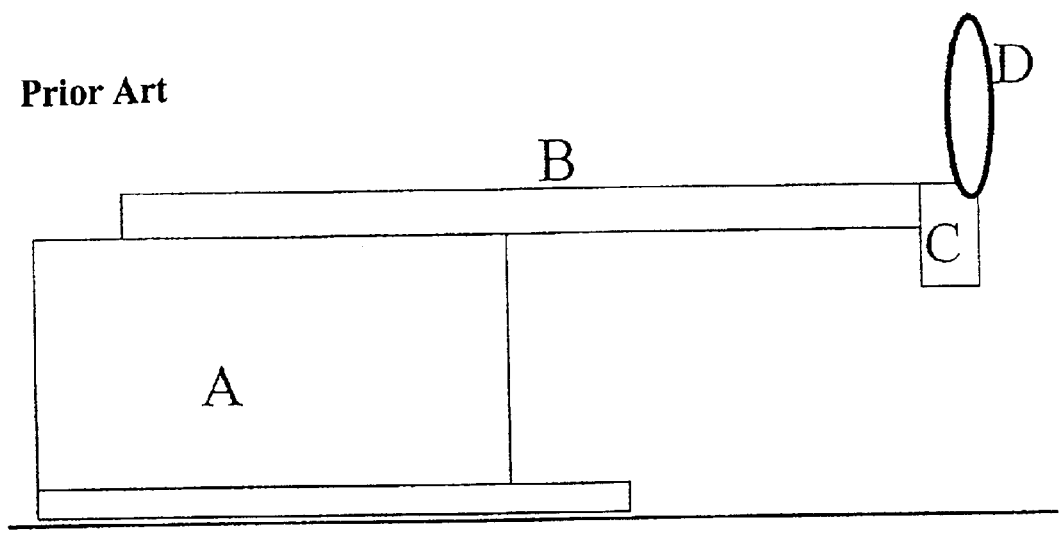

The present invention concerns a patient positioning system for radiotherapy, or for radiation therapy or radiosurgery. In principle, the procedure within the framework of such radiation treatments is that radiation planning is undertaken first of all, wherein image recordings are taken of the patient or of the area of the patient around the radiation target, for example computer tomography recordings. The treatment target is registered via known marking systems. In accordance with the present standard, the patient is then taken off the bed at the image-generating device, and goes independently to the radiotherapy room in order to lie down there on another bed at the radiotherapy apparatus. Here, one attempts via a tracking system to determine the current position of the radiation target, using the position of the markings arranged on the patient, and/or to position the patient by means of a tracking system, such that the treatment target lies in the isocentre of the radiotherapy apparatus. Typically, the image data for planning are not recorded on the same day as treatment takes place.

This approach involves a great disadvantage, alone because of the movement of the patient between the two patient beds. Markings which are mostly arranged on the patient's skin shift during this relocation, in relation to each other and to the radiation target point. Positioning for radiation exposure on the radiotherapy apparatus, and therefore the radiotherapy itself, thus becomes imprecise, which possibly brings the success of the treatment at least partly into question.

A similar problem arises if the position of the radiation target is dependent on the respective breathing state of the patient. If the patient's planning data set, for example, was recorded while the patient was holding his breath, this data set represents the patient and the position of the target volume at a specific lung filling. In order to be able to transfer these data to the state of the patient at the time of radiation exposure, the lung filling would have to exactly correspond at the two points in time. If the patient is able to breathe freely during radiation exposure, this is at most the case at two points in time per breath. Moreover, the breathing drift, being a shift of the underlying lung volume over medium periods of time, will present a problem.

Here too, the problem arises of the transferability of the 3D planning data set to the state of the patient at the time of radiation exposure.

Previous approaches for solving the above latter-mentioned problem have made use of the fact that a patient's breathing may be tracked by observing the outer contour of the thorax and abdomen. If markings are arranged on the patient's skin, these can then be correlated with the position of inner target volumes. However, if the patient is relocated after the image-generating examination (for example CT, MR, SPECT, PET) has been carried out—wherein the patient typically has to get up, walk to the radiotherapy room, and there lie down on another bed—then the sebaceous layers of the patient again slip here, and therefore also the markings arranged on them. This in turn results on the one hand in an inaccurate position of the patient co-ordinate system, as well as to a clear distortion of a possibly previously determined correlation between the breath-dependent position of the target volume and the external markings. For this reason, in accordance with a known approach to solving this problem, correlation is carried out directly, on the radiotherapy apparatus table. This in turn is disadvantageous, because the image-generating methods usable are either of a lower quality compared to the devices described above, or require a high level of investment, since either the therapy device or the image-generating device may be used, but not both at the same time.

It is the object of the invention to solve the problems cited above. This is solved in accordance with the invention by a device as set forth in the enclosed claim 1 and a method as set forth in claim 20, and is based on the one hand on using the same patient bed for positioning the patient on the image-generating device, and for radiation exposure. In other words, the patient can remain lying on one bed, and is taken together with the bed from the planning system to the radiotherapy apparatus. In this way alone, the shifts in an immobilised patient resulting from relocation are considerably reduced. Furthermore, the advantageous accuracy of the system in accordance with the invention is also based on providing a reference means on the transportable patient bed with which the position of the immobilised patient, or of one or more marked reference points on the surface of the patient's body, may be determined with respect to a point fixed on the patient bed. Using this reference means provides an additional fixed reference point near the target volume defined by the markings on the patient and which is very helpful as a fixed positioning quantity, and in particular when a radiation target volume alters its position with the patient's breathing. In previous methods, in which only the position of the patient markings has been used for breath-dependent radiation exposure, an external reference has been lacking which for example would recognise a drift, i.e. a shift in the underlying lung volume. In addition to the unstable relationship between the patient makers and the target volume mentioned above, this could lead to inaccuracies in radiation exposure. Through lack of an external reference, which allows an absolute lung filling co-efficient to be determined, it has accordingly not been possible so far during treatment to allocate triggered image recordings to a defined breathing state.

The fact that such a reference means is now provided on the patient bed in accordance with the invention makes it possible to produce "absolute" patient marker positions, so to speak, with respect to the reference means fixed to the bed. In this way, any shifts in the patient markings between one another, but also with respect to the patient bed system, may be identified and corrected, or considered as to whether these have arisen because the patient has moved, or from breathing movement. Image recordings triggered relative to an absolute lung filling value enable radiation exposure triggered in the course of the treatment with substantially greater precision, i.e. radiation exposure only takes place when the target volume is located at a specified place. In this sense, the present invention helps to avoid positioning errors and to accurately take into account the shifting of organs due to breathing and therefore also allows much more precise and effective radiation exposure than is currently possible in accordance with the prior art.

In a preferred embodiment of the device in accordance with the invention, the device—as already indicated above—comprises a tracking system which can detect both the positions of markings arranged on the patient as well as those of the reference means, in particular of a reference star fitted with an arrangement of markers, on the bed. It should also be stated in particular in this respect that such a reference star, which may for example comprise an arrangement of three infrared reflecting markers, can be observed together with the patient markings during the tomographic imaging (CT) inside the tomography room, so that triggered recordings are possible which then later allow triggered radiation exposure when the patient markers and the markers on the reference star are in a defined relationship, namely +/− a permitted tolerance range around their position (relative to the reference means), during the tomographic imaging. Also conceivable here, as an extension, is taking various planning image recording sets of the same area for a number of defined states (distance ratios) of patient markers and reference markers on the bed, and thus analysing the movement of the target point. The "beam-on range", i.e. the period during which the treatment beam is switched on in the treatment, can then be individually defined for the predetermined marker relationship above. Thus, a complete set of starting points is already available during image recording, i.e. during planning.

In order to be able to implement the invented system, however, it is possibly disadvantageous to only use conventional devices corresponding to the prior art. For this reason, the present invention comprises a new type of patient bed, whose use is itself only possible in conjunction with a new type of angle-adjusting device for positioning the patient during radiation exposure.

The device in accordance with the invention advantageously comprises one or more of the following immobilisation means for immobilising the patient on the patient bed:

vacuum foils with corresponding vacuum pumps elastic bands or foils stretched over the patient vacuum cushions specially fitted to the patient's form thermoplastic body masks specially fitted to the patient's form form cushions or form blocks fitted to the patient's form A device in accordance with the invention for positioning the patient within the framework of treatment planning using image detection and/or performing a radiotherapy treatment, comprising a patient bed on which the patient is positioned, in particular a device as described above, can include an adjusting device with which the patient bed can be rotated about at least two axes, and which is arranged between the patient bed and a supporting device for the patient bed, in particular a planning couch or a treatment table. This tackles the problem that in most cases of image detection and patient irradiation, the angle of rotation about the longitudinal axis of the body and the horizontal lateral axis are not identical in this respect. Therefore, the path which the beam takes to reach the treatment target is in most cases not identical with the path determined during the planning for radiation exposure treatment as the optimum treatment. Stereotactic radiosurgery pre-supposes the possibility of being able to irradiate a specified target area within the patient's body from a specified direction. However, due to the limited rigidity of the tables of linear accelerators and similar radiosurgical and radiotherapeutic systems, it is often the case that the part of the body to be treated, or the entire patient, experiences an angular rotation after having been fixed on the treatment unit, which accordingly has to be corrected. In order to carry out this correction, systems are used in the prior art, in which the head of the patient can be turned laterally or longitudinally within a specified angular range.

Such a patient table system with an adjusting device in accordance with the prior art is shown schematically in FIG. 10. The adjusting device C is fixed to the treatment bed B of the therapy device and receives the head by means of a mask or screw ring system D. In order to achieve the necessary rigidity, these adjusting mechanisms are heavy and relatively large. In order to take the forces and momenta out of their own weight and the weight of the patient's head and to be able to transfer these to the treatment bed, it is necessary to provide relatively solid and heavy absorbing devices on the patient table. However, these absorbing devices are problematic, inasmuch as they cannot be as radioparent as a simple, continuous (carbon) bed. An additional problem is the size of the devices, which significantly increases the risk of collision between the bed and the part of the radiation exposure unit being moved and makes the transport of the bed considerably more difficult. Moreover, the angular adjustment cannot be used for extra-cranial radiation exposure, and it is precisely this deficiency which is a substantial disadvantage due to the recently achieved advancements in the field of extra-cranial radiotherapy.

The device described above solves this problem through by arranging the adjusting device between the patient bed and the supporting unit for the patient bed, i.e. for example the CT couch or the treatment table. In this way, the angular adjustment can be made for all parts of the patient's body, and the adjusting device is no longer in the way during recording, and is no longer a disturbance to the radiotherapy apparatus.

Combination with a detection system (tracking system) is possible.

The adjusting device can enable the patient bed to turn independently about at least one axis laterally and one axis longitudinally to the bed. It preferably consists of a base plate and a cover plate which are movably linked together via a three-point or four-point bearing. It is possible in this connection to design the adjusting device in such a way that it comprises at least two supports which are constructed as height adjustable, pneumatic, hydraulic, piezoelectric or electromechanical supports, adjustable directly or by means of a lever system.

The adjusting device preferably comprises a front, head-end support and a rear, foot-end support, wherein at least one of the supports is constructed as a ball joint or as a universal joint. The front or rear support can in this respect comprise toggle levers with ball joints on both sides.

In an arrangement of the device in accordance with the invention, the bearing of the cover plate on the base plate includes a shaft-groove joint with two translatory and two rotatory degrees of freedom, which prevents the cover plate from shifting laterally with respect to the base plate. On the one hand, the device can comprise adjusting means which cause the bed to rotate about its longitudinal axis by counter-adjusting two head-end or foot-end supports, on the other hand the adjusting means can cause the bed to rotate about its lateral axis by synchronously adjusting one or two head-end or foot-end supports. Both, of course, can be realised. The adjusting means can similarly cause the bed to rotate about its lateral axis by simultaneously adjusting at least one head-end and at least one foot-end support.

Attention must be paid to the adjusting speed, especially when using toggle levers. In one embodiment, the device therefore comprises adjusting means which cause the bed to rotate about its lateral axis by purposefully setting the adjusting speed of at least one head-end and at least one foot-end support, wherein the position of the apparent axis of rotation may be placed in a desired position. The device can further comprise adjusting means which cause the bed to rotate about its longitudinal axis by purposefully setting the adjusting speed of at least two supports, whereby the position of the apparent axis of rotation can be placed in a desired position.

Furthermore, a device is provided in accordance with the invention for positioning the patient within the framework of treatment planning using image detection and/or of carrying out radiation planning, using a patient bed on which a patient is positioned, in particular a device as described above, said device including a transport device, in particular a transport trolley for transporting the bed with the patient lying on it. Such a transport device can optimally supplement the advantageous embodiments of patient positioning as already described above, whereby in a preferred arrangement two latching mechanisms are provided for connecting the patient bed and transport trolley, for attaching the patient bed to a table of a treatment system and to a couch of an imaging planning system. The bed may on the one hand be attached to and detached from the table of a radiotherapy apparatus or the couch of the planning system by adjusting the height of the table or couch; on the other hand, there is also the possibility of realising this by adjusting the height of the transport device.

The invention further provides a method of treatment planning using image detection and/or carrying out a radiation treatment. In this method, the patient is positioned on a patient bed, the same patient bed being used both on a planning couch for image detection within the framework of treatment planning, and also on a radiotherapy table, and the position of the immobilised patient or of a marked radiation target is determined with respect to the patient bed via a reference means which is securely provided on the patient bed. Of course, the method in accordance with the invention also has the advantages over the prior art by way of the device, as already described previously.

In particular, in a method in accordance with the present invention, the bed on which the patient is lying is removed from the planning couch, transported to the radiotherapy apparatus and there re-attached. A tracking system on the imaging device may detect and/or be adjusted to both the position of markings attached to the patient as well as the reference markings on the bed, and can be adjusted in accordance with these. The patient is preferably secured on the bed in such a way that he can neither shift relative to the bed, nor change the position of the parts of his body with respect to one another.

If the method in accordance with the invention is used for breath-synchronised radiation exposure, the secured patient is fitted with external markings, wherein it is verified by way of the position of these markings relative to the reference means that the patient held his breath while the planning data were recorded.

In accordance with a further arrangement of the method in accordance with the invention, the position of patient markings relative to the reference means is determined, and where it corresponds with pre-set figures including tolerances, image recording is started or stopped when the patient holds his breath, starts breathing again, has reached a specified lung filling or exceeds a specified lung filling in a given breath phase (for example, during breathing in or breathing out). Furthermore, it is possible to irradiate the patient only at those times at which the position of patient markings relative to the position of the reference means securely attached to the bed lies within a defined tolerance range about the relative position which obtains while a planning data set is being recorded (triggered radiation exposure).

Figure 1:
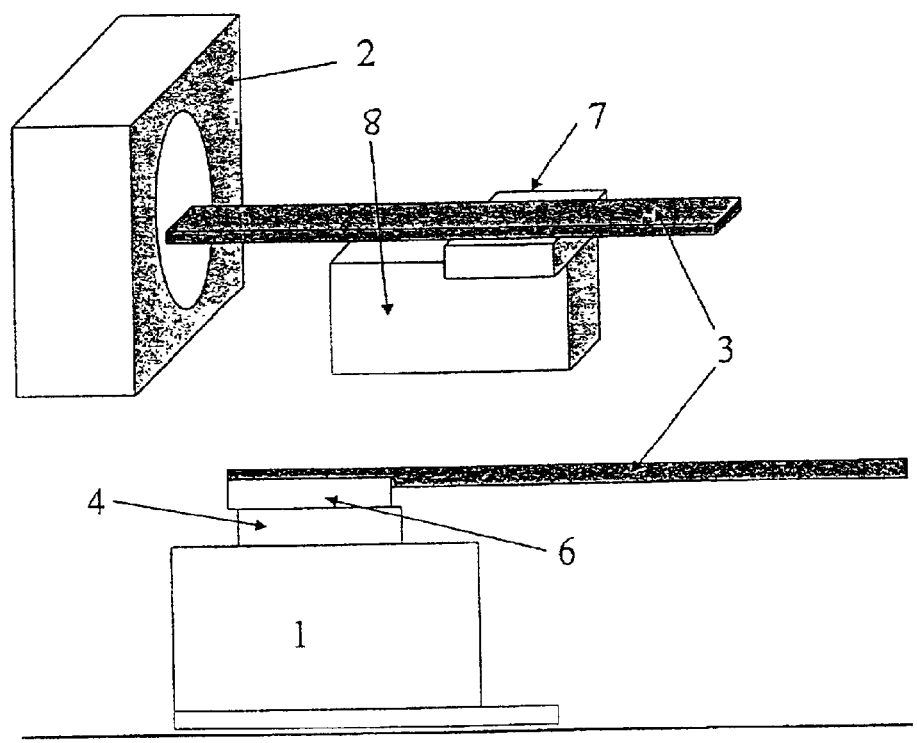
Figure 2:
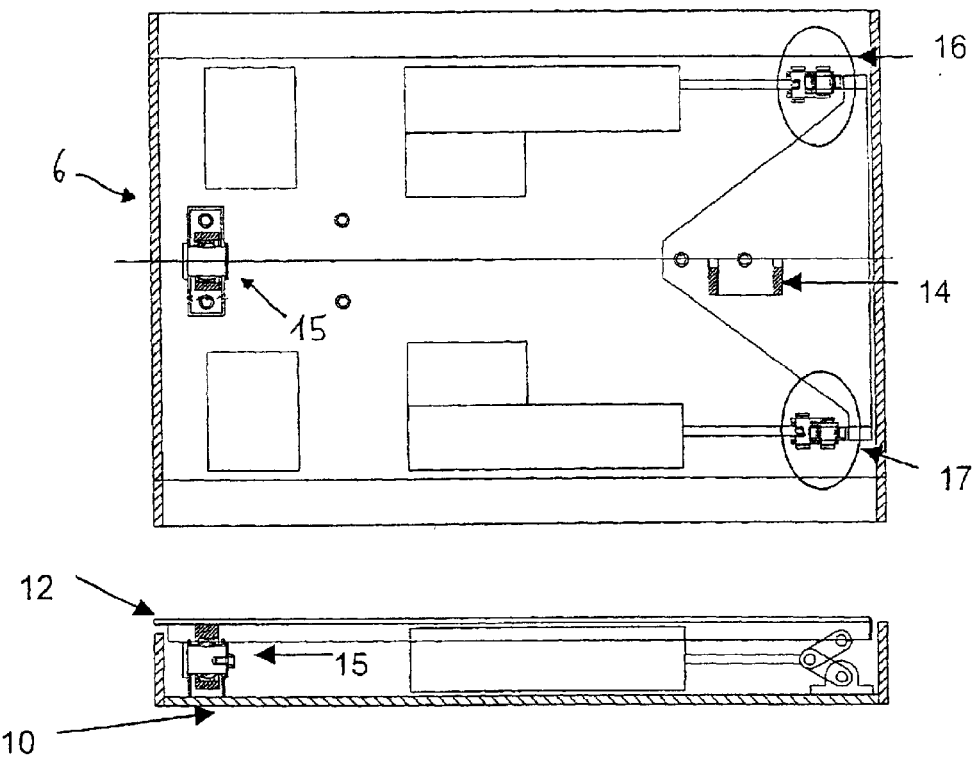
Figure 3:
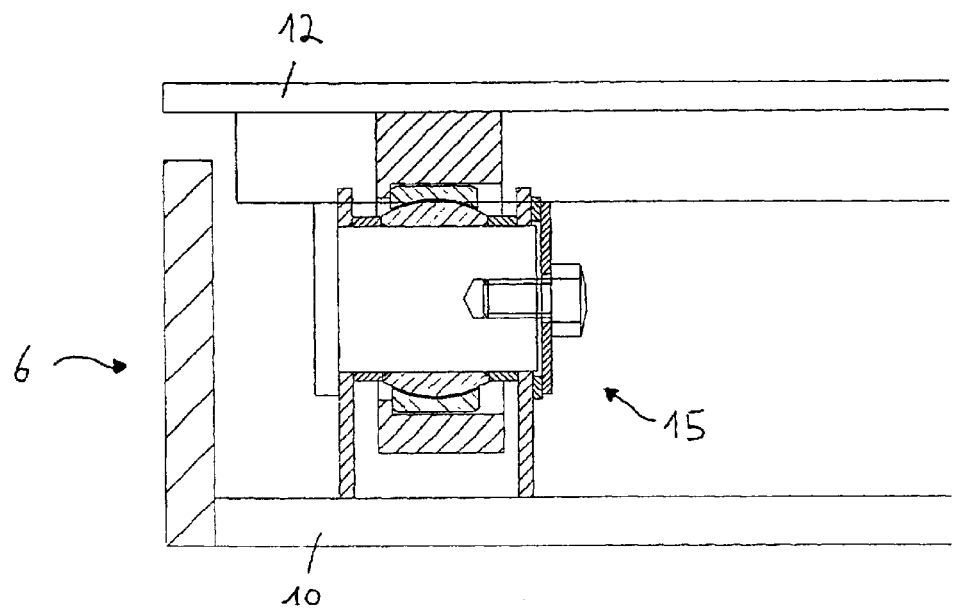
Figure 4:
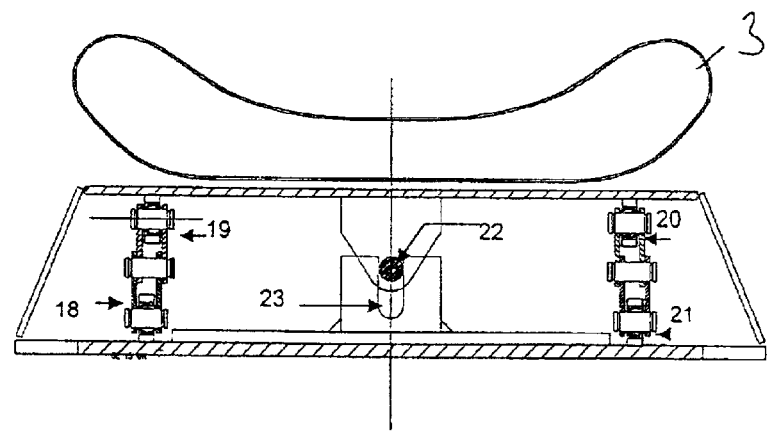
Figure 5:
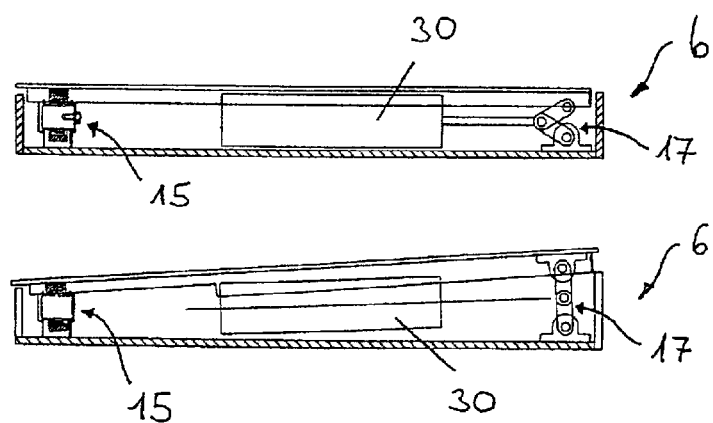
Figure 6:
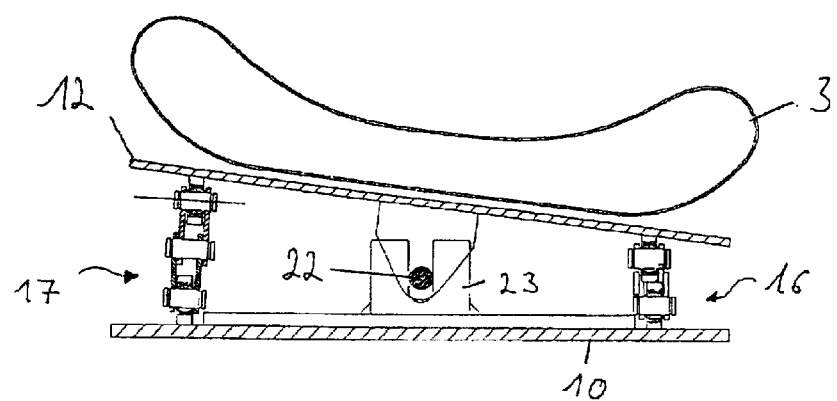
Figure 7:
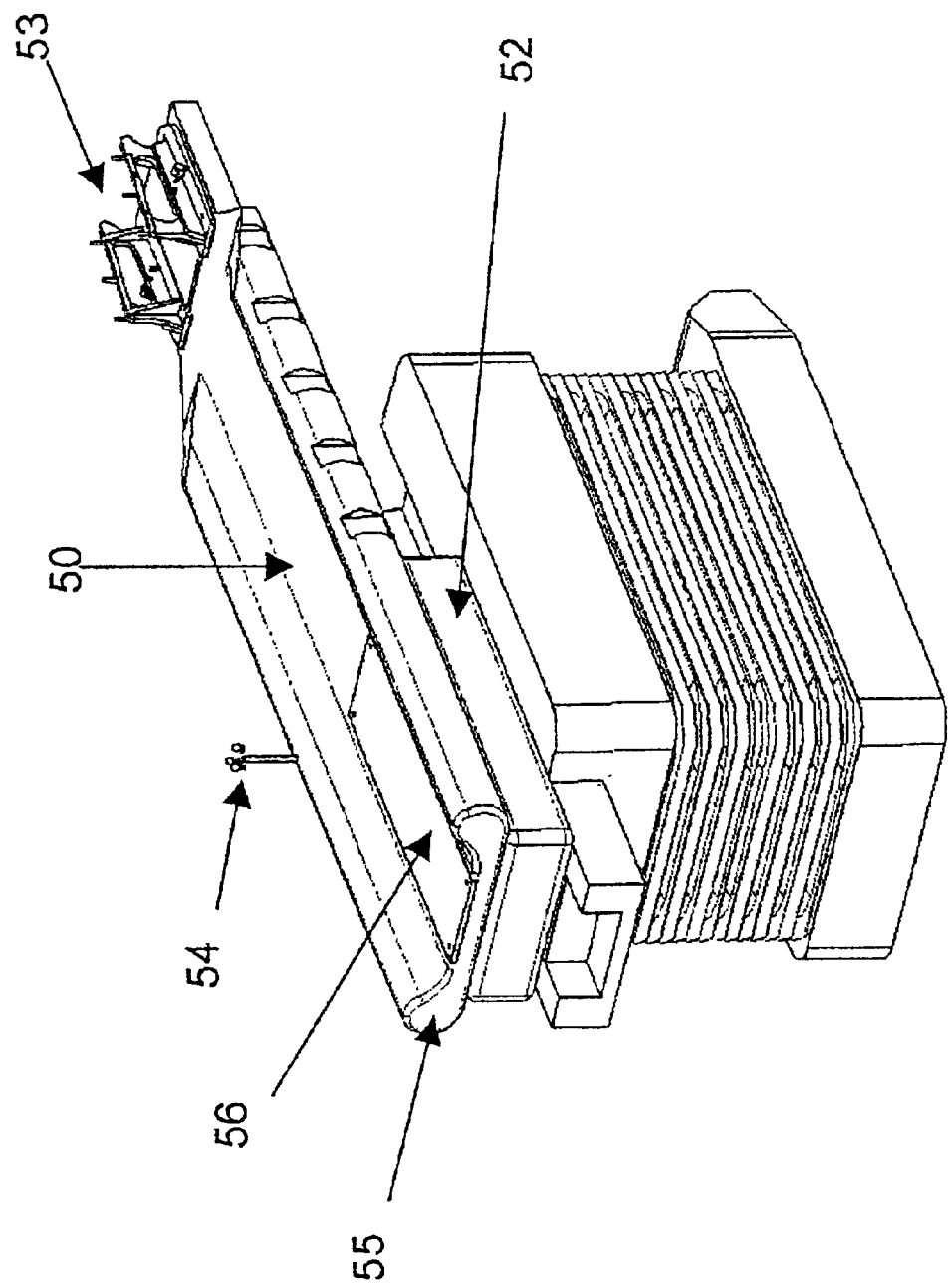
Figure 8:
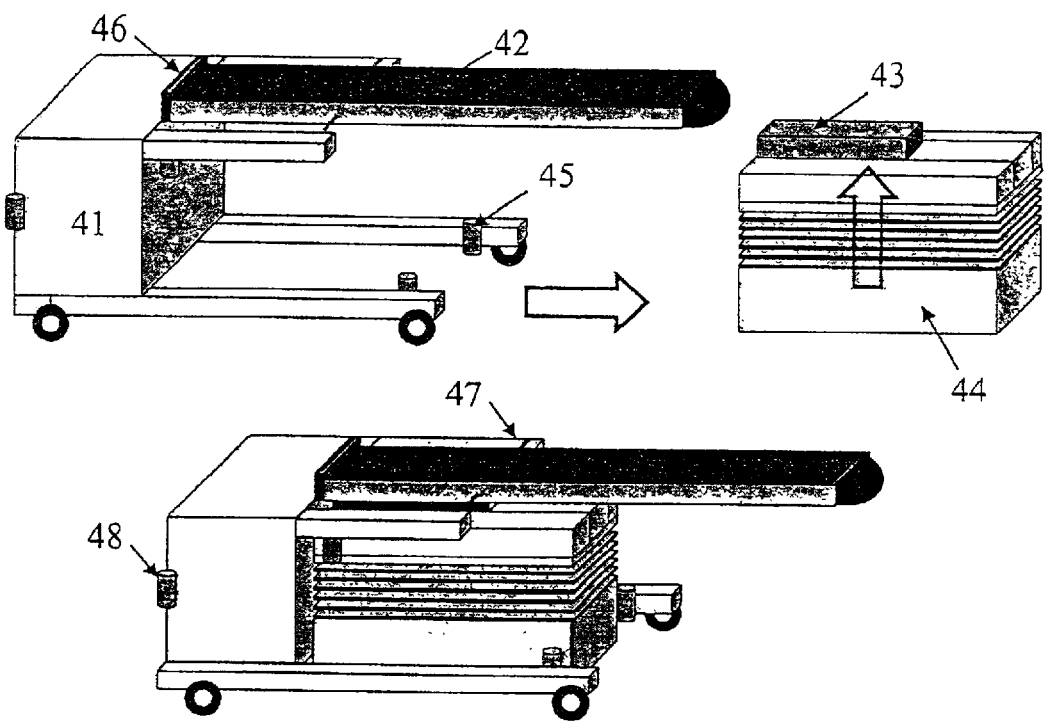
Figure 9:
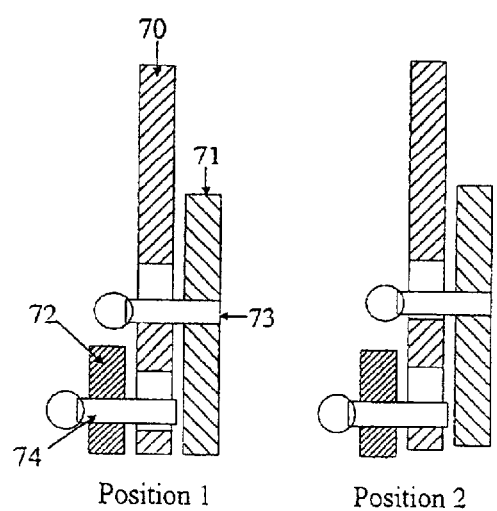

The invention will now be described in more detail by way of preferred embodiments. The enclosed drawings show:

FIG. 1 a patient table—patient bed system with an adjusting device in accordance with the present invention, in an oblique view in an image detection system, and in a side view as it is being used for radiation exposure;

FIG. 2 an adjusting device in accordance with the invention, in an upper and lateral sectional view;

FIG. 3 a rear bearing of the adjusting device, in a lateral, enlarged view;

FIG. 4 a frontal view of an embodiment variant of the adjusting device, comprising two toggle levers and an additional guide joint;

FIG. 5 Sectional side views illustrating a way for the toggle levers of the adjusting device to adjust;

FIG. 6 a frontal view of the adjusting device showing the counter-adjustment of two toggle levers;

FIG. 7 an embodiment variant of a self-supporting carbon bed on the couch of a conventional linear accelerator;

FIG. 8 an embodiment of a transport system for a patient bed;

FIG. 9 an embodiment of a mechanism for latching and releasing the bed on the adjusting device or directly on the couch; and FIG. 10 a schematic diagram of a patient table-patient bed system with an adjusting device in accordance with the prior art.

FIG. 1 shows a patient table-patient bed system with an adjusting device in accordance with the present invention, in an oblique view in an image detection system (planning), and in a side view as it is being used, for example, in radiation therapy under a LINAC (Linear ACcelerator). The upper oblique view (in the planning step) shows: a planning system consisting of a patient couch 8 and an imaging device 2, for example a CT device; and a schematically illustrated latching mechanism 7, with which a patient bed 3 can be fixed to the couch 8. In the lower diagram, the bed 3 for radiation exposure is placed on a patient table 1, and an adjusting device 6 is inserted between a further latching mechanism 4 on the patient table 1 and the patient bed 3.

Instead of the hitherto usual arrangement sequence of the connecting structure: table (A)—bed (B)—adjusting mechanism (C) (see FIG. 10), the connecting structure: table (1, 8)—adjusting mechanism (6)—bed (3) is implemented. Accordingly, the angular correction can also be used for treatment outside of the head area. The second advantage of this procedure is that the bed 3 on which the patient is lying can be constructed throughout from highly radioparent carbon material, even in the neck area; reinforcements, support points and screw points on the patient bed 3 are dropped completely.

Since the system portrayed here is also intended for rigging already existing radiotherapy systems, it is particularly important that the adjusting device 6 can be integrated into a considerably restricted building space. This requirement, however, cannot be realised with conventional systems having two axes of rotation. The system invented therefore uses a special suspension in the adjusting device, a preferred embodiment being described in the following by way of FIG. 2.

FIG. 2 shows an adjusting device 6 in accordance with the invention, in an upper and lateral sectional view. It comprises a base plate 10 and a cover plate 12. The connection between the base plate 10 on the table of the treatment device and the cover plate 12 on which the (carbon) bed 3 is fixed, is realised by a three-point bearing 15, 16, 17, supplemented by an additional lateral guide joint 14. The rear bearing 15 (approximately at the level of the patient's feet) is a ball joint bearing with three rotatory and no translatory degrees of freedom. This is again shown enlarged in FIG. 3. Alternatively, this bearing can be designed as a universal joint.

The front two supports 16, 17 consist of toggle levers which are fixed to the base plate 10 and cover plate 12 respectively with ball joints 18, 19, 20, 21, which can best be seen in the frontal view in FIG. 4.

The side guide joint 14 is located near the centre line between the two toggle levers, and comprises two rotatory and two translatory degrees of freedom. A preferred embodiment of this joint is a shaft 22 which is guided in a slot 23. Alternatively, this joint can also be omitted if a bearing with only two rotatory degrees of freedom is selected on the other side of the mechanism.

FIG. 5 shows sectional side views which illustrate a way for the toggle levers 16, 17 of the adjusting device 6 to adjust, and FIG. 6 shows a frontal view of the adjusting device 6 showing counter-adjustment of two toggle levers 16, 17. The two toggle levers 16, 17 can be guided by electrocylinders (30) (each being a spindle-and-nut system), hydraulic cylinders or pneumatic cylinders.

If the two toggle levers 16, 17 are spread in the same direction, the bed 3 can be turned about an axis perpendicularly to the patient; if the toggle levers 16, 17 are spread in different directions, then rotation about an axis which is approximately parallel to the longitudinal axis of the patient may be realised.

In order to realise rotation about the main axes (the axis through the rear ball joint 15, perpendicular to the symmetry plane of the patient, and the axis parallel to the symmetry plane of the patient), it is necessary to alter the effective height of the toggle levers 16, 17 with an identical and/or reverse speed. Such a counter-adjustment leads, for example, to a state such as shown in FIG. 6. Since the toggle levers 16, 17 exhibit a path and power transmission which is dependent on the buckling angle, it is necessary to guide the toggle levers with different amounts of speeds, calculated depending on the buckling angle of the two toggle levers. If this is realised, then it is possible to turn the bed 3 about the longitudinal axis without changing the angle about the lateral axis or the height of bed 3.

Alternatively, the ball joint 15 can also be designed by a third toggle lever with a one-sided ball joint and a simple rotating bearing on the other side of said toggle lever (not shown). In such an embodiment, the third toggle lever is located in place of the ball joint bearing and is likewise fixed to the base plate and to the cover plate by ball joint bearings. With the aid of said third lever, it is additionally possible to turn the patient about a virtual lateral axis, whose position can be set by the ratio of the effective speeds of the single toggle lever in relation to the effective speed of the two toggle levers on the other side. In this way, it is possible to turn the patient lying on the bed about a specified point, preferably about the point to be treated. In the case of a linear accelerator, this is the isocentre.

FIG. 7 shows a possible embodiment of a patient bed 50 on the adjusting device 6. A head support 53 is shown which cannot be turned and can therefore be realised in very thin and therefore radioparent carbon. An end plate made of metal may be provided as 55, which can serve to fix the bed 50 to an adjusting device 52, or which can also be used to connect foot supports or similar additional devices to the bed 50. Infrared-reflecting markers are arranged on a reference star 54, which can be used as reference markings for markers located on the patient. A frame 56 integrated into the bed is substantially shorter than the actual bed and thereby does not extend into areas which are to be radioparent.

So that the position of the patient on the bed 50 during treatment is the same as that while the planing data set is being recorded, the patient is not allowed to move between these points of time. The bed is therefore preferably combined with a patient fixing system. Suitable for this, among other things, are:
  vacuum foils with corresponding vacuum pumps
  elastic bands or foils stretched over the patient
  vacuum cushions specially fitted to the patient's form
  thermoplastic body masks specially fitted to the patient's form
  form cushions or form blocks fitted to the patient's form The star 54 with the reference markers is securely connected to the bed 50. The patient's breathing changes the distance between the reference markers and possible markers on the patient's thorax. This distance is suitable for describing the patient's breathing. The correlation between this distance value and the position of internal organs of the patient is maintained when the bed 50 is transported, since both the reference markers and the patient are securely connected to the bed. A tracking system (not shown) at the planning location (for example CT) and at the treatment location (LINAC) assists, for example, breath-controlled planning and radiation exposure (triggered CT recordings and triggered radiation exposure), wherein this is only possible because the above-mentioned correlation is maintained. In this respect, a certain tolerance range is also to be maintained. Similarly, the bed 50 is automatically positioned at the LINAC (computer-assisted via the tracking system and the markers on the star 54 on the bed) only when the defined relationship has been reached. It is conceivable as an extension that various CT sets of the same area are recorded at several defined patient-fix-marker states, in order to provide several "starting points" as early as the CT. A physician can then analyse the movement of the target point, and a "beam-on range" during radiation exposure (permissible patient-fix-marker relationship for "beam-on") can be individually defined. In the case of CT planning, this method is to stand only as one example of an imaging method. In principle, the use of other methods is possible, for example MR, SPECT, PET.

In order to be able to make good use of the advantages of a transportable patient bed, it is advantageous to have a device which allows the bed, together with the patient, to be transported from the imaging system to the treatment device. FIG. 8 shows an embodiment of a transport system for a patient bed 42. A transport trolley 41 holds the bed 42 in a broadly horizontal position. When the trolley 41 is moved over the table 44 of the treatment device or of the imaging system, the bed 42 can then be delivered onto the adjusting device 43. The trolley 41 is fitted with side rollers 45 on the inner side of the two lower supports, such that the trolley 41 centres itself automatically with respect to the table 44. The trolley 41 is fitted with side rollers 48 at the end facing away from the bed, so that it is possible to push doors open with the trolley 41.

FIG. 9 shows a possible embodiment of the mechanism for latching and releasing the bed on the adjusting device or directly on the couch. The essential advantage of this mechanism lies in the fact that no significant physical force need be applied, as the force is applied by the table. Both the tables from linear accelerators as well as those from MR and CT systems allow the height of the table to be adjusted. An end plate 70 (reference numeral 46 in FIG. 8), securely connected to the patient bed, is drawn upwards by the torque arising from the weight of the overhanging patient. A bolt 73 connecting the end plate 70 to the adjusting mechanism or the couch 71 is thus constantly loaded with a lateral force. The bolt 73 is preferably constructed with an undercut (not visible in FIG. 9), such that it cannot be withdrawn when it is loaded with a force. A second bolt 74 is guided through the plate 74 connected to the transport means for the bed, into an elongated hole in the end plate 70. As long as the bolt 73 is loaded, the bolt 74 is not loaded, and can therefore be changed without significant physical force. Position 1 shows the situation wherein the bed is connected to the adjusting mechanism (bolt 73 bearing the load).

If the transport system is then moved up to the bed, then moving the table up moves the bed and the adjusting device upwards, and therefore the plates 70 and 71, until the bolt 74 meets at the lower end of the elongated hole, and from then on absorbs the flow of force. If the table is moved a further few millimetres upwards, then the bolt 73 is completely released from the load and may be withdrawn by hand. The bed is detached via the latching mechanism in the reverse of this sequence.

What is claimed is:

1. A device for positioning a patient for treatment planning and radiation treatment comprising:
  a patient bed on which a patient can be positioned,
  a reference device secured to the patient bed that can be tracked by a tracking system,
  wherein the patient bed is configured to be supported by both a planning couch for image-generation and by a radiotherapy table for radiation exposure, and
  whereby the position of the patient and/or of marked points on the surface of the patient's body can be determined with respect to the patient bed.

2. The device as set forth in claim 1, wherein the reference device includes a reference star including an arrangement of markers, and further comprising a tracking system which can detect both the positions of markings arranged on the patient as well as the markers on the reference star.

3. The device as set forth in claim 1, further comprising at least one immobilization device provided to secure the patient to the patient bed.

4. The device as set forth in claim 1, further comprising, an adjusting device configured to be positioned between the patient bed and the planning couch or treatment table such that the patient bed may be rotated about at least two axes.

5. The device as set forth in claim 4, wherein the adjusting device is configured to turn independently about at least one axis laterally and/or one axis longitudinally to the bed.

6. The device as set forth in claim 4, wherein the adjusting device consists of a base plated and a cover plate which are movably linked together via a three-point or four-point bearing.

7. The device as set forth in claim 6, wherein the bearing of the cover plate on the base plate includes a joint with two translatory and two rotatory degrees of freedom, that prevents the cover plate from shifting laterally with respect to the base plate.

8. The device as set forth in claim 4, wherein the adjusting device comprises at least two height adjustable, pneumatic, hydraulic, piezoelectric or electromechanical supports that are adjustable directly or by means of a lever system.

9. The device as set forth in claim 8, wherein the adjusting device is configured to cause the bed to rotate about its longitudinal axis by purposefully setting the adjusting speed of at least two supports, whereby the position of the apparent axis of rotation can be placed in a desired position.

10. The device as set forth in claim 4, wherein the adjusting device comprises a front, head-end support and a rear, foot-end support, wherein at least one of the supports is constructed as a ball joint or as a universal joint.

11. The device as set forth in claim 10, wherein the front or the rear support comprise toggle levers with ball joints on both sides.

12. The device as set forth in claim 10, wherein the adjusting device is configured to cause the bed to rotate about its longitudinal axis by counter-adjusting two head-end or foot-end supports.

13. The device as set forth in claim 10, wherein the adjusting device is configured to cause the bed to rotate about its lateral axis by synchronously adjusting one or two head-end or foot-end supports.

14. The device as set forth in claim 10, wherein the adjusting device is configured to cause the bed to rotate about its lateral axis by simultaneously adjusting at least one head-end and at least one foot-end support.

15. The device as set forth in claim 10, wherein the adjusting device is configured to cause the bed to rotate about its lateral axis by purposefully setting the adjusting speed of at least one head-end and at least one foot-end support, whereby the position of the apparent axis of rotation may be placed in a desired position.

16. A device as set forth in claim 1, further comprising a transport device for transporting the bed with the patient lying on it.

17. The device as set forth in claim 16, further comprising at least two latching mechanisms configured for connecting the patient bed and transport device to a table of a treatment system and to a couch of an imaging planning system.

18. The device as set forth in claim 16, wherein the patient bed can be attached or detached from the table of the radiotherapy apparatus or the couch of the planning system by adjusting the height of the table or couch.

19. The device as set forth in claim 16, wherein the patient bed can be attached or detached from the table of the radiotherapy apparatus or the couch of the planning system by adjusting the height of the transport device.

20. A method for treatment planning using image-generation and carrying out a radiation treatment comprising the steps of:
 positioning a patient on a patient bed,
 securing a reference device to the patient bed,
 supporting the patient bed with a treatment planning couch,
 supporting the patient bed with a radiotherapy table,
 determining the position of the patient or of marked points on the surface of the patient's body with respect to the patient bed using the reference device.

21. The method as set forth in claim 20, wherein the patient bed on which the patient is lying is removed from the planning couch, transported to the radiotherapy apparatus and there re-attached.

22. The method as set forth in claim 20, wherein a tracking system detects the positions of markings arranged on the patient as well as the positions of markers disposed on the reference device.

23. The method as set forth in claim 20, wherein the patient is secured on the bed in such a way that the patient can neither shift relative to the bed, nor change the position of the parts of his body with respect to one another.

24. The method as set forth in claim 20, further comprising the steps of:
 fitting the patient with external markings, and
 determining the position of the external markings relative to the reference device while the patient holds his breath while planning data is recorded.

25. The method as set forth in claim 20, further comprising the steps of:
 determining the positions of the patient markings relative to the reference device,
 comparing the positions with pre-set figures, and
 controlling an image recording based on patient breathing.

26. The method as set forth in claim 20, further comprising the steps of:
 determining the positions of the patient markings relative to the reference device,
 comparing the positions with selected positions obtained when a planning data set is recorded, and
 controlling a radiation treatment based the positions of the patient markings.

* * * * *